United States Patent [19]
Schultz et al.

[11] Patent Number: 5,337,605
[45] Date of Patent: Aug. 16, 1994

[54] ENCLOSURE FOR HUMIDITY SENSING ELEMENT

[75] Inventors: Bruce R. Schultz, West Allis; Kirk P. Henderson, Oconomowoc; Arthur Barootian, Racine, all of Wis.

[73] Assignee: Johnson Service Company, Milwaukee, Wis.

[21] Appl. No.: 7,864

[22] Filed: Jan. 22, 1993

[51] Int. Cl.$^5$ .................... G01N 33/18; B65D 85/00
[52] U.S. Cl. .................... 73/335.02; 73/335.04; 206/305
[58] Field of Search ............ 73/29.02, 335.02, 335.03, 73/335.04, 335.05, 29.05; 422/104; 206/305

[56] References Cited

U.S. PATENT DOCUMENTS

| | | | |
|---|---|---|---|
| 3,168,825 | 2/1969 | Nelson | 73/335.04 |
| 3,350,941 | 11/1967 | Misevich et al. | 73/335.04 |
| 3,712,860 | 1/1973 | Gabrusenok | 73/335.02 X |
| 3,802,268 | 4/1974 | Thoma | 73/335.04 |
| 3,914,982 | 10/1979 | Zanetti | 73/29.02 |
| 4,164,868 | 8/1979 | Suntola | 73/335.04 |
| 4,496,931 | 1/1985 | Watanabe et al. | 73/335.05 X |
| 4,562,725 | 1/1986 | Oka et al. | 73/29.05 |
| 4,655,076 | 4/1987 | Weihe et al. | 73/335.02 X |
| 4,656,455 | 4/1987 | Tanino et al. | 338/35 |
| 4,706,808 | 11/1987 | Guetersloh | 206/305 |
| 4,737,707 | 4/1988 | Mori et al. | 324/689 |
| 4,899,259 | 2/1990 | Voeten | 361/359 |
| 4,920,451 | 4/1990 | Sakai et al. | 361/286 |
| 5,118,981 | 6/1992 | Kobayashi et al. | 310/329 |

Primary Examiner—Robert J. Warden
Assistant Examiner—Robert Carpenter
Attorney, Agent, or Firm—Leonard J. Kalinowski; Joseph E. Root, III; E. L. Levine

[57] ABSTRACT

An enclosure for a film-type humidity sensing element includes identical enclosure members which snap together to form an enclosure with the humidity sensing element sandwiched between the members, each of the members including a lead mounting area on its inner surface for mounting the mounting ends of electrical leads, the leads being connected to contact portions of the humidity sensing element interiorly of the enclosure by a metal-filled conductive adhesive which is introduced into the enclosure through access openings after the enclosure members have been assembled together. The enclosure is adapted for mounting on a circuit board in both horizontal and vertical orientations and independently of the lead structure of the sensor assembly.

15 Claims, 3 Drawing Sheets

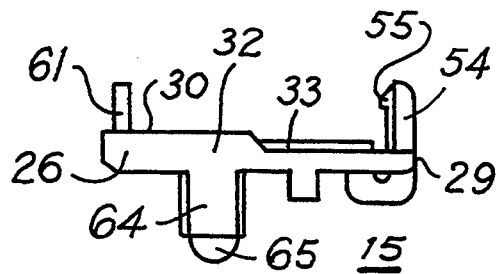
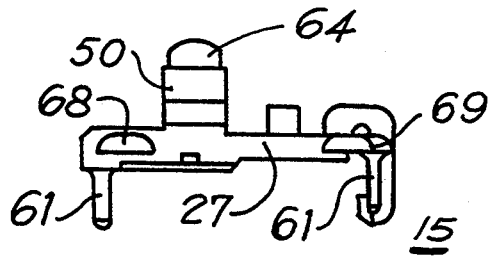
FIG. 7  FIG. 8
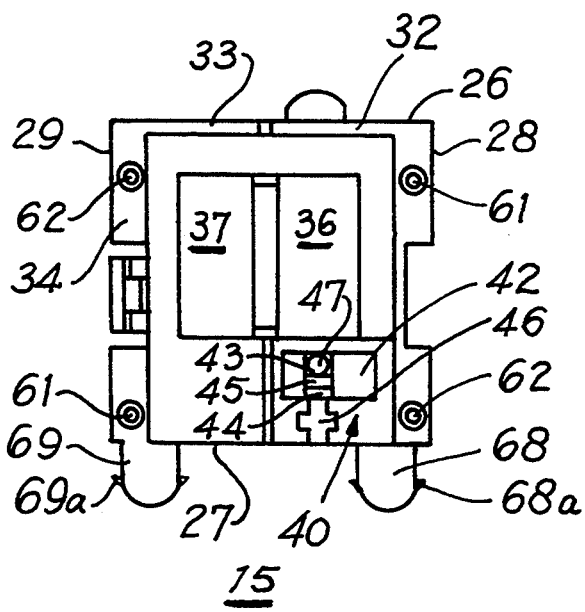
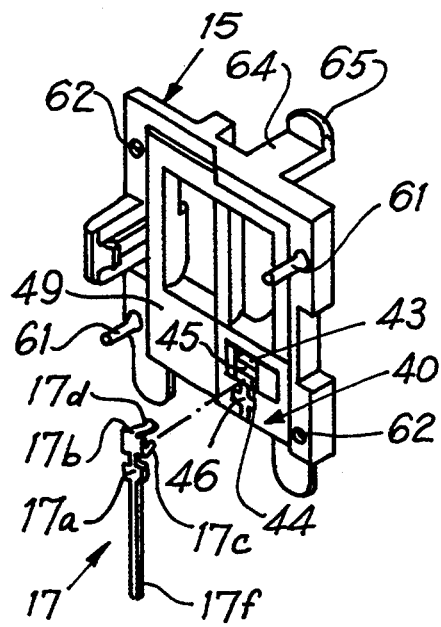
FIG. 9  FIG. 10

ENCLOSURE FOR HUMIDITY SENSING ELEMENT

BACKGROUND OF THE INVENTION

This invention relates to humidity sensor assemblies which include a film-type humidity sensing element, and more particularly, to an enclosure for a film-type humidity sensing element.

Film type capacitive humidity sensing elements include a thin planar dielectric film having conductive coatings disposed on its planar surfaces which are the electrodes for the sensing element. Contact portions are formed on the conductive electrode to facilitate connection of the humidity sensing element to the circuit with which it is used. Film-type humidity sensing elements are very delicate structures which are easily damaged.

Known humidity sensing elements are supported on a base or header by a terminal structure which connects the sensing element in the circuit in which it is used. The sensing element is enclosed by a cover which is mounted on the header. Examples of such sensor assemblies are disclosed in U.S. Pat. Nos. 3,914,982 and 4,920,451. In the sensor assembly disclosed in the '451 patent, the humidity sensing element is carried by the terminals and the cover merely encloses the sensing element. In the sensor assembly disclosed in the '982 patent, the humidity sensing element is mounted in a bearer which in turn is mounted on the terminal bearing header. In both arrangements, the lead structure supports the humidity sensing element, and consequently, the potential exists for damage to the humidity sensing element. A further consideration is that, in use, humidity sensor assemblies of this type are generally mounted on a circuit board by their terminal assemblies which increases the possibility of damage to the humidity sensing element of the assembly.

In U.S. Pat. No. 3,168,829 there is disclosed a capacitive film-type humidity sensor which includes a two part casing which encloses the humidity sensing element and secures the element in the casing by trapping its peripheral edge in an annular groove formed by mating surfaces of the casing members. Although this arrangement affords more protection for the sensing element than is provided by other known prior art sensor assemblies, the casing serves as a portion of the terminal structure and thus must be made of an electrically conductive material. This not only precludes the use of an inexpensive plastic material for the casing, but also requires that the casing be part of the electrical circuit in which the sensor assembly is being used. Moreover, the terminal structure is the primary structure for mounting the sensor assembly in the circuit, and one lead is connected to the sensing element at its unsupported center. Thus, the possibility exists that a force applied to this lead could result in damage to the sensing element.

SUMMARY OF THE INVENTION

It is an object of the invention to provide an improved humidity sensor assembly.

Another object of the invention is to provide a novel enclosure for a film-type humidity sensing element.

A further object of the invention is to provide an enclosure for a film-type humidity sensing element which is inexpensive to produce and which is characterized by ease of assembly.

Another object of the invention is to provide an enclosure for a humidity sensing element which provides strain relief for the leads of the sensing element.

Yet another object of the invention is to provide an a humidity sensor assembly which is adapted for mounting on a printed circuit board in both vertical or horizontal orientations.

These and other objects are achieved by the present invention which provides a humidity sensor assembly which includes a film type humidity sensing element having first and second electrodes each having a contact portion, and an enclosure including first and second enclosure members which are assembled together with the humidity sensing element contained between the enclosure members. The enclosure members have opposing inner surface portions which are spaced apart to define an inner compartment. The enclosure members define first and second lead mounting surface portions located within the enclosure. The sensor assembly further includes first and second electrical leads each having a mounting portion located within the enclosure and secured to a different one of the lead mounting surface portions of the enclosure members. The humidity sensing element is contained within the compartment and secured therein by the opposing surface portions of the enclosure members and with the contact portions of the first and second electrodes located adjacent to the mounting portions of the first and second electrical leads. An electrically conductive means connects the first and second electrical leads, respectively, to the contact portions of the first and second electrodes in the compartment.

Further in accordance with present invention, there is provided an enclosure for a film type humidity sensing element having first and second electrodes each having a contact portion. The enclosure comprises first and second enclosure members adapted to be assembled together with the humidity sensing element contained between the enclosure members. The enclosure members have opposing inner surface portions which are spaced apart to define an inner compartment for containing the humidity sensing element. The enclosure members define lead mounting surface portions within the enclosure for securing mounting portions of electrical leads. The enclosure members have complementary mating inner surface portions with each of the enclosure members having a raised peripheral edge and a recessed peripheral edge portion, the raised peripheral edge portions of the enclosure members being located at opposite sides of the enclosure in engagement with the recessed peripheral edge portions so that the enclosure members are spaced apart from one another to form the compartment.

The invention consists of certain novel features and a conbination of elements fully described, illustrated in the accompanying drawings, and particularly pointed out in the appended claims, it being understood that various changes in the details may be made without departing from the spirit or sacrificing any of the advantages of the present invention.

DESCRIPTION OF THE DRAWINGS

For the purpose of facilitating and understanding the invention, there is illustrated in the accompanying drawings a preferred embodiment thereof, from an inspection of which, when considered in connection with the following description, the invention, its construction and operation, and many of its advantages will be readily understood and appreciated.

FIG. 7 is a top view of the enclosure member;

FIG. 8 is a bottom view of the enclosure member;

FIG. 9 is a rear view of the enclosure member;

FIG. 10 is a perspective view of one of the enclosure members illustrating the mounting of a lead thereto;

DESCRIPTION OF THE PREFERRED EMBODIMENT

Figure 1:
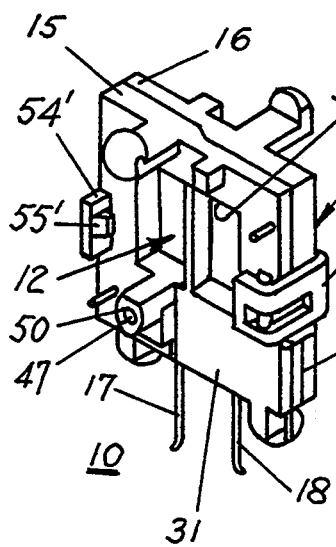
FIG. 1 is a perspective view of a humidity sensor assembly provided by the present invention.
Figure 2:
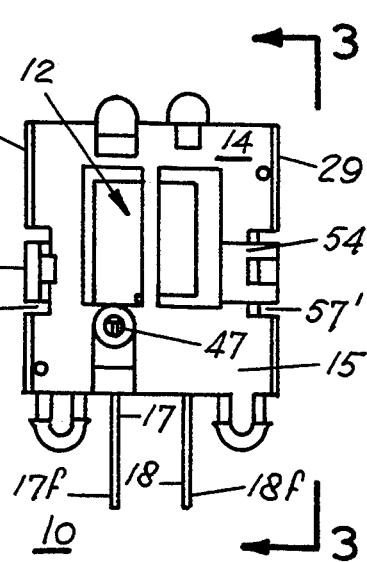
FIG. 2 is a front elevation view of the humidity sensor assembly provided by the present invention.
Figure 3:
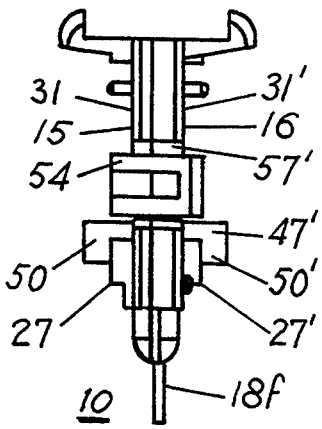
FIG. 3 is a side elevation view of the humidity sensor assembly provided by the present invention.
Figure 4:
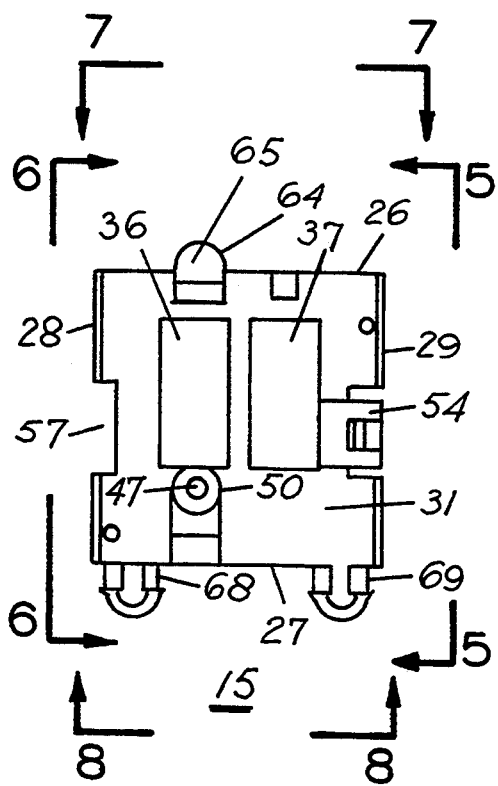
FIG. 4 is a front view of one of the enclosure members of the enclosure.
Figure 5:
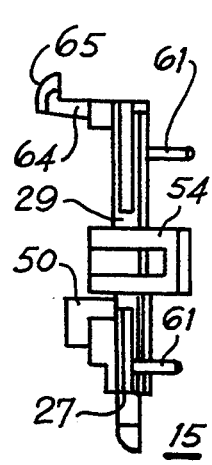
FIG. 5 is a right side view of the enclosure member shown in FIG. 4.
Figure 6:
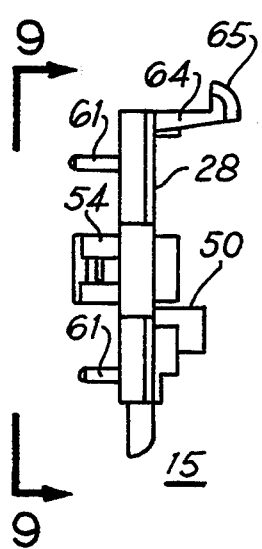
FIG. 6 is a left side view of the enclosure member.

Referring to FIGS. 1–3 of the drawings, the humidity sensor assembly 10 provided by the present invention includes a film-type humidity sensing element 12, an enclosure 14, including a pair of enclosure members 15 and 16, and a pair of electrical leads 17 and 18 which are connected to the humidity sensing element internally of the enclosure 14. The two enclosure members 15 and 16 are adapted to snap together with the humidity sensing element and mounting portions of the electrical leads contained between the two enclosure members. The enclosure members secure the humidity sensing element within the enclosure independently of the lead structure. The enclosure members, when assembled together, also protect the humidity sensing element and provide strain relief for the electrical leads.

Figure 11:
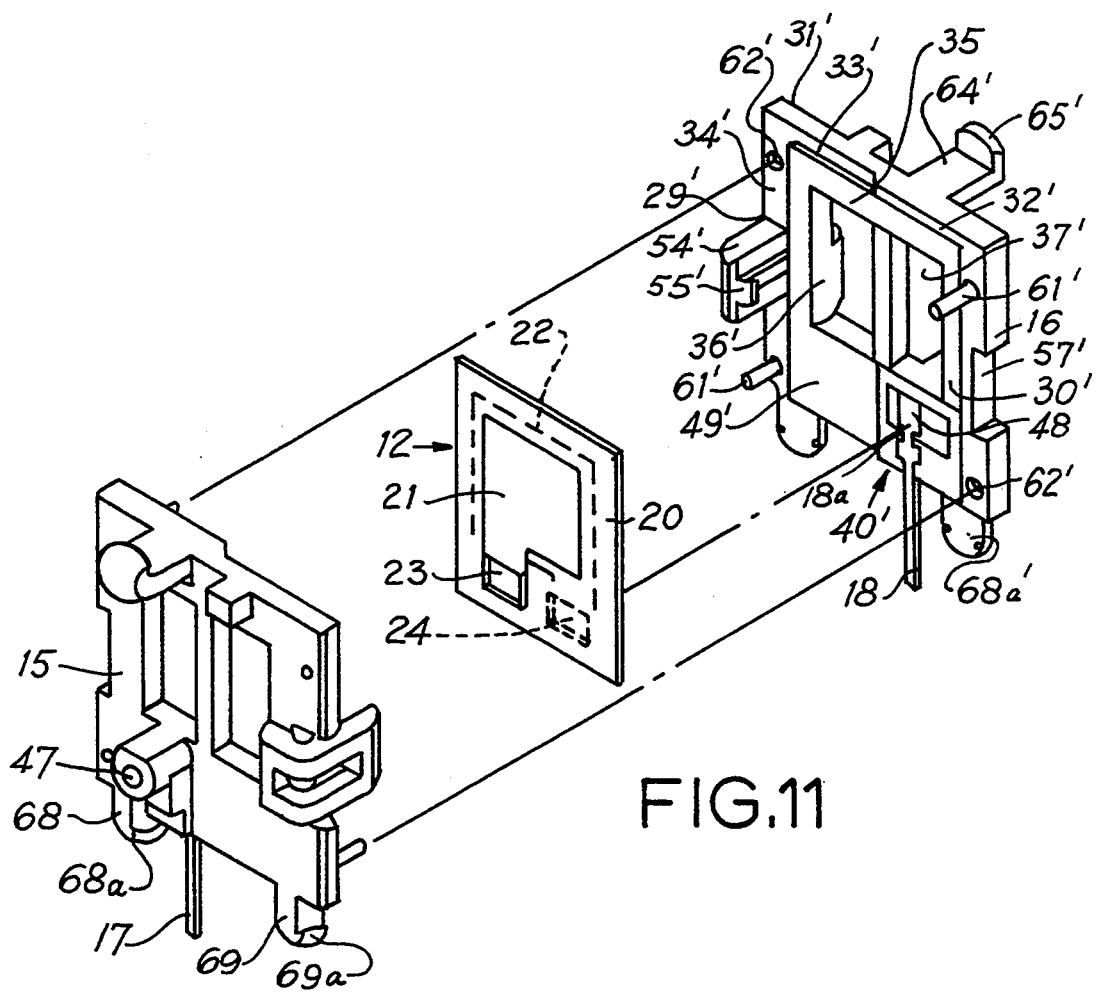
FIG. 11 is an exploded perspective view of the humidity sensor assembly provided by the present invention.

Referring additionally to FIG. 11, the humidity sensing element 12 is constructed on a 0.3 mil polyimide dielectric foil or film 20. Carbon-loaded polysulfone conductor plates 21 and 22 are screen-printed on the surfaces of the film and fused to the film. Silver-loaded polysulfone contact pads 23 and 24 are screen-printed and fused to the conductive plates.

The mating enclosure members 15 and 16 are flat, generally rectangular members which are identical in dimensions and in configuration. Accordingly, only enclosure member 15 is described in detail and elements of enclosure member 16 have been given the same reference numeral as corresponding elements of enclosure member 15, but with a prime notation.

Referring to FIGS. 4–9, enclosure member 15 has an upper edge 26, a lower edge 27, and side edges 28 and 29. The enclosure member 15 has a generally planar inner surface 30 and a generally planar outer surface 31. Preferably, the enclosure members 15 and 16 are molded from a rigid, non-hydroscopic plastic material.

Enclosure member 15 has an inwardly directed ridge 32 on its inner surface 30 which extends along side 28 and along approximately one-half the extent of its upper edge 26. The remaining portion 33 of the upper edge of enclosure member 15 is cut back or recessed as shown in FIG. 7. The enclosure member 15 is stepped down along its side 29 defining a shoulder or recessed portion 34. Digressing, with reference to FIG. 11, when the two enclosure members 15 and 16 are assembled together, the raised portions 32 and the recessed portions 33 and 34 of enclosure member 15 mate with complementary surface portions, recessed portions 33' and 34' and raised portions 32' of enclosure member 16. The height of the raised portions 32 and 32' is greater than depth of the recessed portions so that when the enclosure members are assembled together, the opposing inner surfaces of the enclosure members define an inner compartment 35 in which the humidity sensing element 12 is contained and secured within the enclosure 14.

Enclosure member 15 has two openings or windows 36 and 37 to permit air flow across the humidity sensing element 12 allowing the sensing element to sense moisture in the air moving across the faces of the sensing element 12. The openings 36 and 37 are sufficiently large as to expose substantially the entire sensing element 12 to air flow, except for its peripheral mounting edges and its lower edge portion that includes contact pads 23 and 24 which are located in the lead mounting area 40 of the enclosure 14. The large openings 36 and 37 permit quick response to the sensing element 12 to air movement at the faces of the humidity sensing element 12.

Referring to FIGS. 4, 6 and 9–11, the enclosure member 15 has a lead mounting area 40 on its inner surface 30 which is adapted to receive and secure the mounting end 17a of electrical lead 17. The lead mounting portion 40 includes a raised portion 41 and a recessed portion 42, both of which are rectangular in shape. The recessed portion 42 includes rectangular-shaped cavities 43 and 44 which are separated by a wall 45. The raised portion 41 includes a T-shaped indentation 46 which corresponds is size and shape to a portion of the lead mounting end 17a. As shown in FIG. 10, the lead mounting portion 17a includes resilient mounting tabs 17b, 17c and 17d which straddle the wall 45. Tabs 17b and 17c are located in side-by-side relation and tab 17d is located forwardly of tabs 17b and 17c, spaced apart a distance that is slightly less than the width of the wall 45. The mounting tabs are spring loaded to grip the wall 45 when the lead mounting end 17a is positioned in the lead mounting surface area 40, securing the lead 17 to the mounting surface 40. The lead mounting end 17a has two lateral projections 17e which lie in the indentation 46 when the lead is secured to the mounting surface 40. The lead 17 has a terminal portion 17f which extends out of the enclosure 14 between the lower edges 27 and 27' of the enclosure members as shown in FIG. 3.

The electrical connections, as well as the bonding of the lead mounting end 17a to the enclosure 14 is effected by applying a metal-filled conductive adhesive to the lead mounting surfaces 40 and the juxtaposed contact portions and lead ends. This insures electrical conductivity between the contact portions of the humidity sensing element 12 and the lead because the lead connection area is potted with the conductive metal-filled adhesive. This potting also prevents corrosion and or degradation of the connection because the adhesive seals the lead to the contact portions of the humidity sensing element 12. The leads 17 and 18 are retained in the enclosure 14 to allow ease of assembly and to provide a strain relief feature in the completed sensor assembly 10.

The conductive adhesive may be applied to the juxtaposed contact portions of the sensing element and the lead mounting ends at each lead mounting area 40 prior to assembling the enclosure members together or after the enclosure members 15 and 16 have been assembled together. To this end, with reference to FIGS. 4–10, a through bore 47 is provided through the enclosure member 15 from the base of the cavity 43 and through a cylindrical projection 50 on the outer surface 31, providing access to the lead mounting area 40 from the exterior of the enclosure 14. The bore 47 serves as an access opening to permit electrical connections to be made between the contact portions 23 and 24 of the humidity sensing element 12 and the mounting end 17a of the lead. Alternatively, a metal-filled conductive adhesive can be applied to the juxtaposed contact portions and lead mounting ends prior to assembling the enclosure members together and then a non-conductive encapsulant can be introduced into the junction area through the access openings 47 and 47' for potting the lead connections after the enclosure members have been assembled together.

The metal-filled conductive adhesive bonds the contact pads 23 and 24 of the humidity sensing element to the leads 17 and 18 to ensure good electrical contact and to encapsulate the lead element connections. Additionally, the conductive adhesive also mechanically bonds the terminals 17 and 18 to the lead mounting surfaces 40 and 40' of the associated enclosure members 15 and 16. One metal-filled conductive adhesive suitable for this application is an electrically conductive, silver-filled epoxy adhesive. Conductive epoxy adhesive provides good mechanical and electrical properties. It develops strong, durable, electrically and thermally conducting bonds and coatings between the metal leads and the contact pads. The compound cures at room temperature and is thus can be used as a cold solder to interconnect the lead and contact pad electrically and mechanically. Although one type of metal-filled conductive adhesive has been described, other types of conductive adhesive may be used including epoxy adhesives filled with other conductive metals, adhesives which cure at temperatures other than room temperature, and conductive adhesives other than epoxy.

Referring to FIGS. 1–3, 5, and 7, for the purpose of securing the enclosure member 15 to the enclosure member 16, the enclosure member 15 includes a resilient catch element 54 on its edge 29 and a notch 57 on its other edge 28. The catch element 54 projects rearwardly and passes through a complementary notch 57' of enclosure member 16. The catch element 54 has an inwardly directed tab 55 which engages the outer surface 31' of enclosure member 16 when the enclosure members 15 and 16 are assembled together. Similarly, the catch element 54' of the other enclosure member 16 passes through the notch 57 on edge 28 of the enclosure member 15 and its distal tab 55 (FIG. 1) engages the outer surface 31 of enclosure member 15 when the enclosure members are assembled together.

The enclosure member 15 includes alignment pins 61 located at diametrically opposed corners of the element and a recessed holes 62 located at the other diametrically opposed corners. Pins 61 are received in mating holes 62' of enclosure member 16 and holes 62 receive the alignment pins 61' of the other enclosure member 16. The alignment pin and hole pairs permit easier assembly by guiding the enclosure members 15 and 16 together during assembly.

In accordance with a feature of the invention, the humidity sensor assembly 10 is adapted for mounting on a circuit board in both horizontal and vertical orientations and independent of the terminal structure. To this end, the enclosure members 15 and 16 include mounting elements which facilitate the securing of the enclosure to the circuit board.

More specifically, with reference to FIGS. 4–8, and 12–13, the enclosure member 15 has a resilient catch element 64 for mounting the sensor assembly on a circuit board 70 in a horizontal orientation. Catch element 64 projects forwardly from the outer surface 31 of the enclosure member 15 near its upper edge 26. Catch element 64 has a hook 65 formed at its distal end. The catch element 64 cooperates with the cylindrical projection 50 of the enclosure member 15 to secure the sensor assembly 10 to a circuit board 70. The enclosure member 15 also has a pair of mounting legs 68 and 69 depending from its lower edge 27 for mounting the sensor assembly 10 on a circuit board in a vertical orientation. The mounting legs 68 and 69 have distal tips 68a and 69a flared slightly to engage the undersurface of the circuit board 70. These circuit board mounting features prevent the transfer of stress to the sensing element 12 and the element lead connection, providing a more reliable connection.

Referring to FIG. 10, in assembling the humidity sensor assembly 10, first the leads 17 and 18 are mounted on the respective enclosure members 15 and 16. As shown in FIG. 10, lead 17 is positioned overlying the lead mounting area 40 of the enclosure member 16 with its mounting tabs 17b–17d being extended into the cavities 43 and 44, to straddle the wall 45. This secures the lead 17 to the enclosure member 15. The lead 18 is mounted on enclosure member 16 in the same manner.

Referring now to FIG. 11, then the humidity sensing element 12 is placed on one of the enclosure members, enclosure member 16 in the exemplary embodiment, with its contact portion 24 overlying the lead mounting end 18 which is located in the lead mounting area 40'. The conductive adhesive may be applied to the contact portion 24 and the lead mounting end 18a (and to contact portion 23 and lead mounting end 17a) prior to assembling the enclosure members together. A small quantity of conductive adhesive 48 is shown in FIG. 11 applied to lead mounting end 18a. The conductive adhesive is also applied to lead mounting end 17a. The conductive adhesive is distributed around the contact portions and lead mounting ends and the mounting area when the enclosure members are assembled together. The enclosure member 15, with terminal 17 secured thereto, is positioned over the sub-assembly of the humidity sensing element 12 and enclosure member 16 with the alignment pins 61 aligned with alignment holes 62' in the enclosure member 16 and with alignment holes 62 aligned with alignment pins 61' of enclosure member 16. Then, the enclosure member 15 is moved into place so that the catch elements 54 and 54' of the two elements engage and their respective tip portions 55 and 55' flex around the outer surfaces 31 of the enclosure members to lock the two enclosure members together.

The relative sizes of the raised portions 32, 32' and the recessed portions 33, 33', 34 and 34' are such that the spacing between the opposing inner surfaces of the enclosure members 15 and 16 corresponds to the thickness of the film 20 and conductors 21 and 22 so that the sensing element 12 is held loosely by the mating enclosure members, and independently of the lead connections. Also, the opposing inner surface portions of the enclosure members in the lead mounting area secure the lead mounting end thereat between the mating enclosure members. In particular, the lead mounting areas, such as area 40 for enclosure member 15, define recessed surface portions which receive the lead mounting portions, and the opposing surface portion 49' of the mating enclosure member 16 is flat and planar and engages the raised part 41 of the lead mounting surface 40 and the upper surface of the lead mounting end located thereat, firmly holding the lead mounting end in place.

If the conductive adhesive is applied after the enclosure members have been assembled together, the metal-filled conductive adhesive is introduced into the interior of the enclosure through the two access openings 47 and 47' to connect and bond the leads 17 and 18 to the contact pads 23 and 24 of the film humidity sensing element 12. By way of example, the metal filled conductive adhesive may be contained in syringe (not shown) which has a tip that can be inserted into the access openings 47 and 47' in the enclosure 14. The curing time and curing temperature are a function of the adhesive used.

Figure 12:
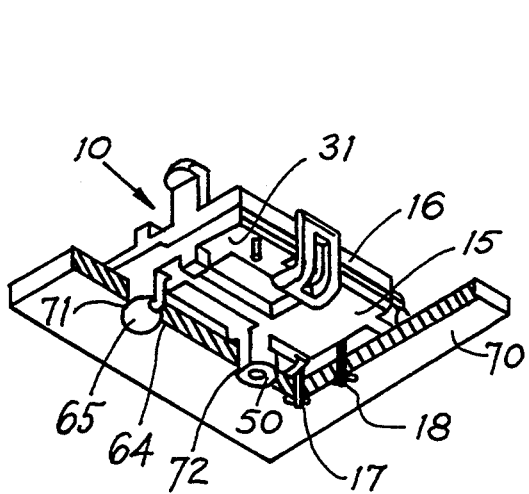
FIG. 12 is a perspective view illustrating the mounting of the humidity sensor assembly on a printed circuit board in a horizontal orientation; and, FIG. 13 is a view similar to FIG. 12, but illustrates the mounting of the humidity sensor assembly on a printed circuit board in a vertical orientation.

Referring to FIG. 12, the sensor assembly 10 is shown mounted on a circuit board 70 in a horizontal orientation. The catch element 64 is received in an aperture 71 in the circuit board and the cylindrical extension 50 extends into a further aperture 72 in the circuit board 70. As the catch element 64 is being inserted into the aperture 71, its rounded distal tip portion 64a rides along the peripheral edge of the aperture 71, urging the hook portion 65 inwardly, i.e., toward the lower edge 27 of member 15, until the broad distal tip has passed through the board at which time, the hook portion 65 flexes back to its normal position, and engages the underside of the circuit board.

Figure 13:
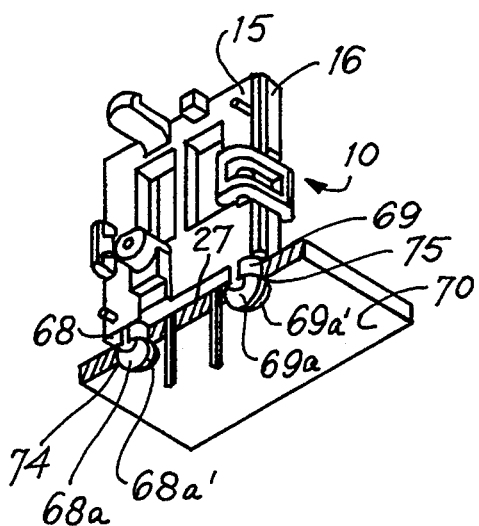

Referring to FIG. 13, the sensor assembly 10 is shown mounted on the circuit board 70 in a vertical orientation. The sensor assembly 10 is positioned with its lower edge 27 adjacent to the circuit board 70 and with its mounting legs 68 and 69 overlying apertures 74 and 75 in the circuit board 70. Then, the mounting legs 68 and 69 of the sensor assembly 10 are pushed into the apertures 74 and 75, with the flared tips 68a, 69a, 68a' and 69a' engaging the underside of the circuit board 70 to secure the humidity sensor assembly 10 to the circuit board 70.

We claim:

1. A humidity sensor assembly comprising:
   a film humidity sensing element having first and second electrodes each having a contact portion, said humidity sensing element having a peripheral edge;
   an enclosure including first and second mating enclosure members assembled together with said humidity sensing element contained between said enclosure members; said first and second enclosure members having opposing inner surface portions which are spaced apart to define an inner compartment, said opposing inner surface portions of said first and second enclosure members defining first and second lead mounting surfaces located within said enclosure;
   first and second electrical leads each having a mounting portion located within said enclosure and secured to a different one of said lead mounting surfaces;
   said humidity sensing element being contained within said compartment with said peripheral edge engaged by said opposing inner surface portions of said enclosure members and with said contact portions of said first and second electrodes located adjacent to said mounting portions of said first and second electrical leads;
   and electrically conductive means for connecting said first and second electrical leads, respectively, to said contact portions of said first and second electrodes in said compartment,
   the spacing between said opposing inner surface portions of said enclosure members corresponding substantially to the thickness of said humidity sensing element at least at said peripheral edge, whereby said humidity sensing element is secured in said enclosure by said mating enclosure members and independently of the lead connections.

2. The sensor assembly according to claim 1, wherein each of said enclosure members has at least one opening therethrough to admit moisture to said humidity sensing element.

3. The sensor assembly according to claim 1, wherein said enclosure members are identical to each other in dimensions and configuration.

4. The sensor assembly according to claim 3, wherein said enclosure members are generally rectangular in shape.

5. The sensor assembly according to claim 4, wherein said enclosure members have complementary mating inner surface portions, including a raised peripheral edge portion and a recessed peripheral edge portion for each enclosure member, the height of said raised peripheral edge portions being greater than the depth of said recessed peripheral edge portions whereby when said first and second enclosure members are assembled together with their inner surfaces opposing one another, the raised and recessed peripheral edge portions of said first enclosure member mate with respective complementary shaped recessed and raised peripheral edge portions of said second enclosure member so that opposing inner surface portions of said first and second enclosure members are spaced apart from one another to form said compartment.

6. The sensor assembly according to claim 1, wherein said lead mounting surfaces are defined by recessed portions of said opposed inner surface portions of said enclosure members.

7. The sensor assembly according to claim 1, wherein said conductive means comprises a metal-filled conductive adhesive which electrically and mechanically connects said mounting portions of said leads to said contact portions of said electrodes and mechanically connects said mounting portions of said leads to said lead mounting surfaces of said enclosure.

8. The sensor assembly according to claim 7, wherein each of said enclosure members has an access opening which communicates said lead mounting surfaces with the exterior of said enclosure to permit said metal-filled conductive adhesive to be introduced into said inner compartment while said enclosure members are assembled together to connect and bond said mounting portions of said leads to said contact portions of said electrodes.

9. The sensor assembly according to claim 1, wherein said first and second enclosure members each include alignment means for aligning said first enclosure member with said second enclosure member, said alignment means comprising a plurality of pin and hole pairs on said enclosure members.

10. The sensor assembly according to claim 9, and including fastening means for securing said first and second enclosure members together, said fastening means including a catch member on each of said enclosure members and a complementary notch on each of said enclosure members.

11. The sensor assembly according to claim 1, wherein each of said enclosure members includes a resilient arm and an extension portion which project outwardly from its outer surface and are adapted to cooperate with apertures in a circuit board for securing said enclosure to the circuit board in a horizontal orientation.

12. The sensor assembly according to claim 1, wherein each of said enclosure members includes extension portions depending from the lower edge of said member and adapted to cooperate with apertures in a circuit board for securing said enclosure to a circuit board in a vertical orientation.

13. The sensor assembly according to claim 1, wherein said enclosure members are made of a non-hydroscopic plastic material.

14. A humidity sensor assembly comprising:
a film humidity sensing element having first and second electrodes each having a contact portion, said humidity sensing element having a peripheral edge;
and an enclosure including first and second mating enclosure members assembled together with said humidity sensing element contained between said enclosure members,
said first and second enclosure members being rectangular in shape and identical to each other in dimensions and configuration,
said first and second enclosure members having mating opposing inner surface portions which are spaced apart to define an inner compartment,
said humidity sensing element being contained within said compartment with its peripheral edge engaged by said mating inner surface portions of said enclosure members, whereby said humidity sensing element is secured in said enclosure by said mating opposing inner surface portions of said enclosure members, and wherein said inner surface portions of each of said enclosure members defines a recessed lead mounting surface which is located within said enclosure for locating an electrical lead relative to one of said contact portions of the humidity sensing element.

15. The sensor assembly according to claim 14, wherein said enclosure members each has an upper edge, a lower edge and first and second side edges, and said enclosure members are assembled together with said upper edge, said lower edge and said first and second side edges of said first enclosure member located adjacent to said upper edge, said lower edge and said second and first side edges, respectively, of said second enclosure member.

* * * * *